US012564555B2

(12) United States Patent
Muzzio et al.

(10) Patent No.: US 12,564,555 B2
(45) Date of Patent: Mar. 3, 2026

(54) CONTINUOUS PROCESSES FOR MANUFACTURING IMPREGNATED POROUS CARRIERS AND FOR MANUFACTURING PHARMACEUTICALS CONTAINING IMPREGNATED POROUS CARRIERS

(71) Applicant: Rutgers, The State University of New Jersey, New Brunswick, NJ (US)

(72) Inventors: Fernando J. Muzzio, Sparta, NJ (US); Benjamin J. Glasser, Princeton, NJ (US); Thamer A. Omar, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 746 days.

(21) Appl. No.: 17/756,738

(22) PCT Filed: Dec. 15, 2020

(86) PCT No.: PCT/US2020/065085
§ 371 (c)(1),
(2) Date: Jun. 1, 2022

(87) PCT Pub. No.: WO2021/126829
PCT Pub. Date: Jun. 24, 2021

(65) Prior Publication Data
US 2023/0000776 A1      Jan. 5, 2023

Related U.S. Application Data

(60) Provisional application No. 62/948,477, filed on Dec. 16, 2019.

(51) Int. Cl.
*A61K 9/16*       (2006.01)
*A61K 31/192*    (2006.01)

(52) U.S. Cl.
CPC .......... *A61K 9/1682* (2013.01); *A61K 9/1611* (2013.01); *A61K 9/1652* (2013.01); *A61K 31/192* (2013.01)

(58) Field of Classification Search
None
See application file for complete search history.

(56) References Cited

U.S. PATENT DOCUMENTS

| | | |
|---|---|---|
| 5,055,307 A | 10/1991 | Tsuru et al. |
| 6,103,255 A | 8/2000 | Levene et al. |
| 6,136,288 A | 10/2000 | Bauer et al. |
| 7,569,274 B2 | 8/2009 | Besse et al. |
| 9,078,756 B2 | 7/2015 | Gatt et al. |
| 2003/0017189 A1 | 1/2003 | Wong et al. |
| 2008/0026057 A1 | 1/2008 | Benke |
| 2009/0017125 A1 | 1/2009 | Lynenskjold et al. |
| 2009/0162435 A1 | 6/2009 | Bunick et al. |
| 2009/0202649 A1 | 8/2009 | Gore et al. |
| 2009/0298847 A1 | 12/2009 | Jeon et al. |
| 2010/0055133 A1 | 3/2010 | Duffield et al. |
| 2011/0064805 A1 | 3/2011 | Obae et al. |
| 2013/0053446 A1 | 2/2013 | Muzzio et al. |
| 2014/0378401 A1 | 12/2014 | Horn |
| 2016/0193033 A1 | 7/2016 | Murray et al. |
| 2017/0157049 A1 | 6/2017 | Dandl et al. |
| 2017/0281615 A1 | 10/2017 | Gaik et al. |
| 2017/0312226 A1 | 11/2017 | Gumudavelli et al. |
| 2018/0263896 A1 | 9/2018 | Muzzio et al. |
| 2019/0192946 A1 | 6/2019 | Demkowski et al. |

(Continued)

FOREIGN PATENT DOCUMENTS

| | | |
|---|---|---|
| AU | 2009224418 A2 | 10/2010 |
| EP | 0266113 | 5/1988 |
| EP | 1493404 A1 | 1/2005 |

(Continued)

OTHER PUBLICATIONS

Kukkar et al., "Mixing and formulation of low dose drugs: underlying problems and solutions", Thai Journal of Pharmaceutical Sciences, Dec. 31, 2008, pp. 43-58.

Nguyen et al., "Protein Powders for Encapsulation: A Comparison of Spray-Freeze Drying and Spray Drying of Darbepoetin Alfa.", Pharmaceutical Research, vol. 21, No. 3, Mar. 2004, p. 507.

Keleb et al: "Cold extrusion as a continuous single-step granulation and tabletting process", European Journal of Pharmaceutics and Biopharmaceutics, Elsevier Science Publishers B.V., Amsterdam, NL, Nov. 1, 2001 (Nov. 1, 2001), vol. 52, No. 3, pp. 359-368, XP004311175, ISSN: 0939-6411, DOI: 10.1016/S0939-6411(01)00195-3.

Becker et al: "Solvent-Free Melting Techniques for the Preparation of Lipid-Based Solid Oral Formulations", Environmental Science and Pollution Research, Springer Berlin Heidelberg, Berlin/Heidelberg, Mar. 19, 2015, vol. 32, No. 5, pp. 1519-1545, XP035444577.

Breitenbach, Jörg: "(Melt extrusion: from process to drug delivery technology", European Journal of Pharmaceutics and Biopharmaceutics, 2002, 54, pp. 107-117.

(Continued)

*Primary Examiner* — Robert A Wax
*Assistant Examiner* — Andre Mach
(74) *Attorney, Agent, or Firm* — FOX ROTHSCHILD LLP

(57) ABSTRACT

The present disclosure relates to a continuous process for impregnating active pharmaceutical ingredients (API) onto porous carriers, including the steps of introducing a porous carrier into a first feeder; continuously directing the porous carrier from the first feeder into a continuous blender, wherein the continuous blender comprises one or more nozzles; continuously introducing a solution comprising an API dissolved in solvent into the continuous blender through the one or more nozzles to form API-impregnated porous carrier; and continuously drying the API-impregnated porous carrier using a fluidized bed dryer to form a powder. The present disclosure also relates to a continuous process for manufacturing pharmaceutical drug products using continuously manufactured API-impregnated porous carriers. The present disclosure also relates to a continuous pharmaceutical drug manufacturing process that includes API-impregnated porous carriers as a raw material.

19 Claims, 3 Drawing Sheets

(56) References Cited

U.S. PATENT DOCUMENTS

| | | |
|---|---|---|
| 2020/0024736 A1 | 1/2020 | Gangakhedkar et al. |
| 2024/0390285 A1 | 11/2024 | Muzzio et al. |

FOREIGN PATENT DOCUMENTS

| | | | | |
|---|---|---|---|---|
| EP | 2870960 A1 | 5/2015 | | |
| JP | 2018507180 A | 3/2018 | | |
| WO | 1997/047290 | 12/1997 | | |
| WO | 2004/022037 | 3/2004 | | |
| WO | 2005/034908 | 4/2005 | | |
| WO | 2007/086846 A1 | 8/2007 | | |
| WO | 2007086646 A1 | 8/2007 | | |
| WO | 2008/014175 | 1/2008 | | |
| WO | 2009/113522 | 9/2009 | | |
| WO | 2009/132411 A1 | 11/2009 | | |
| WO | 2009/135646 | 11/2009 | | |
| WO | 2010094471 A1 | 8/2010 | | |
| WO | WO-2012027222 A1 * | 3/2012 | .............. | A61K 9/00 |
| WO | WO-2013091006 A1 * | 6/2013 | ........... | A61K 9/0075 |
| WO | 2014194872 A1 | 12/2014 | | |
| WO | 2015193485 A1 | 12/2015 | | |

OTHER PUBLICATIONS

Censi et al: "Hot Melt Extrusion: Highlighting Physicochemical Factors to Be Investigated While Designing and Optimizing a Hot Melt Extrusion Process", Pharmaceutics, 2018, 10, 89:27 pages. doi: 10.3390/pharmaceutics10030089.

Crowley et al: "Pharmaceutical Applications of Hot-Melt Extrusion: Part I", Drug Development and Industrial Pharmacy, 2007, 33(9), pp. 909-926, DOI: 10.1080/03639040701498759.

Passerini et al: "Preparation and characterization of ibuprofen-poloxamer 188 granules obtained by melt granulation", European Journal of Pharmaceutical Sciences 15 (2002) pp. 71-78.

Repka et al: "Applications of Hot-Melt Extrusion For Drug Delivery", Expert Opin Drug Deliv., Dec. 2008, 5(12), pp. 1357-1376. doi:10.1517/17425240802583421.

Repka et al: "Melt extrusion: process to product", Expert Opinion on Drug Delivery, 2012, 9:1, pp. 105-125. DOI: 10.1517/17425247.2012.642365.

Repka et al: "Melt extrusion with poorly soluble drugs—An integrated review", Int J Pharm. Jan. 15, 2018, 535 (1-2): 68-85. doi:10.1016/j.ijpharm.2017.10.056.

Sacher et al: "Towards a novel continuous HME-Tableting line: Process development and control concept", European Journal of Pharmaceutical Sciences, Jan. 15, 2020 (online Oct. 21, 2019), vol. 142, pp. 1-14.

U.S. Department of Health and Human Services Food and Drug Administration Center for Drug Evaluation and Research (CDER): "Waiver of In Vivo Bioavailability and Bioequivalence Studies for Immediate-Release Solid Oral Dosage Forms Based on a Biopharmaceutics Classification System Guidance for Industry". Retrieved from the internet on Apr. 30. URL: <https://digirepo.nlm.nih.gov/master/borndig/101720038/UCM070246.pdf>; 2017: 19 pages.

Becker et al: "Solvent-Free Melting Techniques for the Preparation of Lipid-Based Solid Oral Formulations", Pharm Res, 2015, 32, pp. 1519-1545. DOI: 10.1007/s11095-015-1661-y.

* cited by examiner

CONTINUOUS PROCESSES FOR MANUFACTURING IMPREGNATED POROUS CARRIERS AND FOR MANUFACTURING PHARMACEUTICALS CONTAINING IMPREGNATED POROUS CARRIERS

CROSS-REFERENCE TO RELATED APPLICATION

This application is a U.S. National Phase of International Patent Appl. No. PCT/US20/65085 filed Dec. 15, 2020, which claims the benefit of priority to U.S. Provisional Patent Appl. No. 62/948,477 filed Dec. 16, 2019, the disclosures of which are hereby incorporated by reference in their entireties.

FIELD

The disclosed technology relates to a continuous process for impregnating active pharmaceutical ingredients (API) onto porous carriers, a continuous process for manufacturing pharmaceutical drug products using continuously manufactured API-impregnated porous carriers, and a continuous pharmaceutical drug manufacturing process that includes API-impregnated porous carriers as a raw material.

BACKGROUND

Oral pharmaceutical products, e.g., tablets and capsules, are often manufactured in a batch processing manner, whereby the drug products are made according to a single manufacturing sequence that includes a series of unit operations, such as blending, granulating, milling, tableting, etc. In general, batch manufacturing is a step-by-step process requiring multiple pieces of equipment to implement each unit operation, and each unit operation on any given batch typically must finish before the next batch can be processed. In contrast, in continuous manufacturing, only a small portion of the production lot is being processed at any given time, the material flows continuously from each unit operation to the next, and all unit operations proceed simultaneously. Because continuous processes are operated at or near a steady state, and because only a small amount of material is being processed at any given time, continuous processes typically achieve higher productivity, better quality, better product uniformity, lower labor costs, and more stable and reliable processes than their batch counterparts.

Additionally, a common problem in pharmaceutical product development is how to form homogeneous blends containing small amounts of highly potent pharmaceuticals. With some approaches (e.g., direct blending, wet and dry granulation), as the drug concentration decreases, the variability of the blend increases. This problem is further aggravated when the drug is poorly soluble.

A large percentage of APIs and new chemical entities have been reported as being poorly water-soluble. In general, poorly water-soluble APIs present challenges such as poor absorption and low bioavailability, which makes it is difficult to deliver the API into a subject's blood stream. The US Pharmacopeia describes the solubility of drugs in terms of the number of milliliters of solvent in which one gram of solute will dissolve. Typically, drugs defined as "poorly soluble" are those that require more than 1 ml of solvent per 10 mg of solute. The Biopharmaceutics Classification System (BCS) divides drugs into the following four groups with respect to solubility and permeability: Class I (high solubility, high permeability), Class II (low solubility, high permeability), Class III (high solubility, low permeability), and Class IV (low solubility, low permeability). According to the BCS, a drug substance is considered "poorly soluble" or of low solubility when more than 250 mL of an aqueous solution in a pH range of 1.2 to 6.8 at 37±1° C. is required to solubilize the highest single therapeutic dose. Permeability is evaluated with respect to the extent of absorption of a drug from human pharmacokinetic studies. A drug is considered "highly permeable" when its absolute bioavailability is greater than or equal to 85%. Among the four BCS groups, drugs in Classes II and IV exhibit poor aqueous solubility, resulting in poor bioavailability. Such poorly soluble drugs also often exhibit uneven absorption, with the degree of unevenness being influenced by factors such as dose level, patient satiety, and drug form, as well as a number of other parameters affecting the product manufacturing process.

A poorly soluble drug often needs to be micronized, but reduction in particle size increases the drug tendency to agglomerate. When the drug dose is low, agglomerates can cause significant fluctuations in unit dose potency, often leading to substantial content uniformity issues. One method for addressing uniformity of low-dose oral solid products is described in U.S. Pat. No. 10,004,682, wherein a drug solution/suspension is impregnated throughout the volume of a batch of porous carrier by spraying the solution/suspension onto the carrier in a fluid bed processor operated in batch mode. Following spraying, the solvent is subsequently evaporated, providing a composite particle of the carrier and the drug(s). The dried carrier is highly uniform, as would be evidenced by unit dose sampling and subsequent testing. The dried carrier can be subsequently milled to further improve uniformity, and then filled into capsules, aerosol blisters, or compressed into tablets.

Given the rapidly growing interest in continuous pharmaceutical manufacturing, it is highly desirable to be able to impregnate porous carriers in a continuous manner, to create homogenous blends containing small amounts of active pharmaceutical ingredients (APIs), to improve the efficiency of drug product development, to develop methods that are more robust and more readily controlled, and to find commercially valuable alternatives to batch processing for pharmaceutical product development for situations where the existing continuous processes (direct compression, wet granulation, roller compaction) are unable to handle such situations efficiently.

SUMMARY

The present disclosure generally relates to a method for continuously impregnating a porous carrier, the use of that method in the manufacture of pharmaceutical drug products, and the use of API-impregnated porous carriers as a raw material in a continuous pharmaceutical drug manufacturing process. Continuous manufacturing, in contrast to traditional batch processing, allows for the manufacturing of drug products from raw materials in a single continuous fashion such that the output is maintained at a consistent rate with no need to stop production. As a result, the disclosed technology is capable of efficiently providing highly homogenous pharmaceutical drug products containing small amounts of API in a robust, readily controlled, and commercially valuable manufacturing process.

In the instant invention, it has been surprisingly discovered that an efficient continuous impregnation process can be created by impregnating the carrier in a continuous blender, and subsequently drying it in a continuous drier.

In one aspect, the disclosed technology relates to a continuous process for manufacturing API-impregnated porous carrier, including: (a) introducing porous carrier into a controlled flow feeder; (b) continuously directing the porous carrier from the controlled flow feeder into a continuous blender, wherein the continuous blender includes one or more nozzles; (c) continuously spraying a solution/suspension including one or more active pharmaceutical ingredients (APIs) dissolved/suspended in a volatile solvent into the continuous blender through the one or more nozzles, to form API-impregnated porous carrier; and (d) continuously drying the API-impregnated porous carrier using a continuous dryer to form dry API-impregnated porous carrier in powder form. In one embodiment, content variability of any single API in the powder has a relative standard deviation (RSD) of less than or equal to 3% when tested using samples of at least 200 mg of the dried API-impregnated porous carrier powder. In another embodiment, the porous carrier is directed into the continuous blender in step (b) at a feed rate from 1 kg/h to 200 kg/h. In another embodiment, the API solution is sprayed into the continuous blender in step (c) at a rate of less than 1 s$^{-1}$. In another embodiment, the continuous dryer of step (d) is a fluidized bed dryer that includes an air inlet stream having a temperature of 30° C. to 90° C. In another embodiment, the porous carrier is selected from magnesium aluminum metasilicate, granulated silicon dioxide, dibasic calcium phosphate, calcium hydrogen phosphate, and combinations thereof. In another embodiment, the porous carrier has a porosity of 20% to 85% pores by volume. In another embodiment, the porous carrier has an average pore size of 100 nm to 2000 nm. In another embodiment, the continuous process produces API-impregnated porous carrier powder that releases 50% of the API faster than a non-impregnated dry blend in powder form of the API and the porous carrier powder, where no solvent has been used. In another embodiment, the suspension/solution might contain a wetting agent to facilitate impregnation. In yet another embodiment, a controlled release polymer is also suspended or dissolved in the solution/suspension to modulate the release rate of the one of more APIs from the carrier. In yet another embodiment, a stabilizer is also suspended or dissolved in the solution/suspension to achieve superior chemical stability of the impregnated carrier and of the products manufactured using the impregnated carrier.

In another aspect, the disclosed technology relates to a continuous process for manufacturing a pharmaceutical drug product from continuously manufactured API-impregnated porous carrier, including: (a) introducing porous carrier into a first feeder; (b) continuously directing the porous carrier from the first feeder into a continuous blender, wherein the continuous blender includes one or more nozzles; (c) continuously spraying a solution including an active pharmaceutical ingredient (API) dissolved in solvent into the continuous blender through the one or more nozzles to form API-impregnated porous carrier; (d) continuously drying the API-impregnated porous carrier using a fluidized bed dryer to form API-impregnated porous carrier powder; and (e) formulating the API-impregnated porous carrier powder into a finished pharmaceutical drug product. In one embodiment, the finished pharmaceutical drug product is a solid oral dosage form. In another embodiment, the solid oral dosage form can be a tablet, capsule, powder, or a granulate. In another embodiment, additional continuous impregnation and continuous drying steps are implemented to create a composite with desirable properties. In another embodiment, the impregnated carrier is continuously coated to provide desirable properties. In another embodiment, step (e) further includes combining the powder with one or more pharmaceutically acceptable excipients selected from carriers, fillers, extenders, binders, humectants, disintegrating agents, absorption accelerators, wetting agents, controlled release agents, absorbents, lubricants, stabilizers, and coloring agents.

In another aspect, the disclosed technology relates to a continuous process for manufacturing a pharmaceutical drug product using the active pharmaceutical ingredient (API) impregnated porous carrier as an ingredient, including: (a) continuously feeding the API-impregnated porous carrier into a first controlled flow feeder; (b) optionally, continuously combining the API-impregnated porous carrier with one or more pharmaceutically acceptable excipients in a continuous blender to form a mixture, and (c) continuously compounding the API-impregnated porous carrier and the optional additional ingredients into a solid oral dosage form, which can be optionally subsequently coated either using a batch or a continuous coating process. In some embodiments, the API-impregnated porous carrier is capable of flowing through a feeder at a feed rate of 1 kg/h to 200 kg/h. In one embodiment, the solid oral dosage form is selected from a tablet, capsule, powder, and granulate. In another embodiment, the process is operated under closed loop control using a combination of sensors, controllers, and actuators to maintain the process within a desired range of operating parameters and/or material attributes. In another embodiment, the API-impregnated porous carrier is also prepared by a continuous manufacturing process. In another embodiment, the API-impregnated porous carrier is prepared prior to its use in the continuous process by a batch manufacturing process.

In another aspect, the disclosed technology relates to a finished pharmaceutical drug product, including an active pharmaceutical ingredient (API) impregnated porous carrier and one or more pharmaceutically acceptable excipients, wherein the finished pharmaceutical drug product has one or more of the following properties: content variability of any single API in the finished pharmaceutical drug product has a relative standard deviation (RSD) of less than or equal to 3% when tested using single doses of the pharmaceutical drug product; the finished pharmaceutical drug product is a solid oral dosage form; and the finished pharmaceutical drug product releases 50% of the API faster than a pharmaceutical drug product that differs only by having been made with a dry blend of API and porous carrier instead of using the API-impregnated carrier. In one embodiment, the solid oral dosage form is selected from a tablet, capsule, powder, and granulate.

A variety of additional aspects will be set forth in the description that follows. The aspects can relate to individual features and to combinations of features. It is to be understood that both the foregoing general description and the following detailed description are exemplary and explanatory only and are not restrictive of the broad inventive concepts upon which the embodiments disclosed herein are based. The person of ordinary skill in the art, with a practical understanding of pharmaceutical formulation, pharmaceutical manufacturing, and continuous processing, would know how to use the invention disclosed here, in combination with routine experiments, to achieve additional variations in composition of matter, manufacturing process, and product formulation methods.

BRIEF DESCRIPTION OF THE DRAWINGS

The accompanying drawings, which are incorporated herein and constitute part of this specification, are illustrative of particular embodiments of the present disclosure and do not limit the scope of the present disclosure. The drawings are not to scale and are intended for use in conjunction with the explanations in the following detailed description.

DETAILED DESCRIPTION

Figure 1:
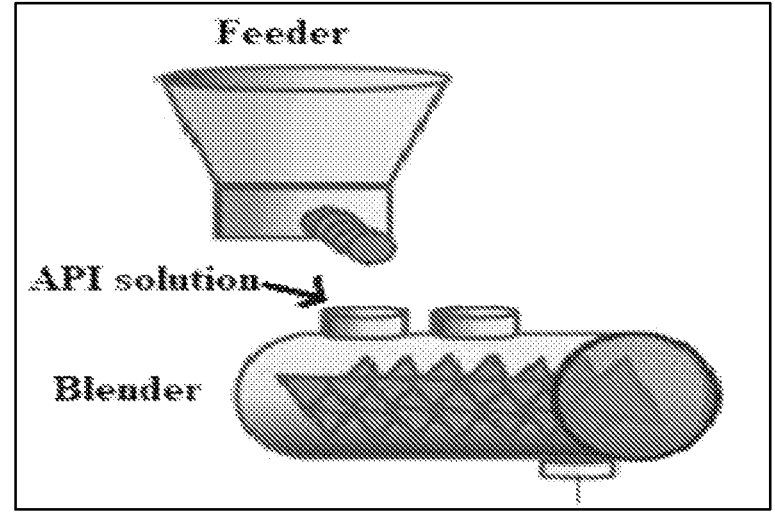
FIG. 1 shows an example schematic of a portion of the disclosed continuous manufacturing process for the impregnated carrier, including porous carrier in a first controlled flow feeder which is fed into a continuous blender into which API solution/suspension is sprayed in order to form particles of API-impregnated porous carrier.

The following discussion omits or only briefly describes conventional features of the disclosed technology that are apparent to those skilled in the art. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations. A person of ordinary skill in the art would know how to use the instant invention, in combination with routine experiments, to achieve other outcomes not specifically disclosed in the examples or the embodiments.

Unless otherwise specifically defined herein, all terms are to be given their broadest possible interpretation including meanings implied from the specification as well as meanings understood by those skilled in the art and/or as defined in dictionaries, treatises, etc. Unless defined otherwise, all technical and scientific terms used herein have the same meaning as commonly understood by one of ordinary skill in the art in the field of the disclosed technology. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof. Additionally, methods, equipment, and materials similar or equivalent to those described herein can also be used in the practice or testing of the disclosed technology.

In the disclosed process, continuous impregnation can be either a stand-alone process for manufacturing API-impregnated carrier, or can be part of a larger integrated continuous manufacturing line for manufacturing of pharmaceutical products containing API-impregnated carrier. Continuous manufacturing methods can provide significant technical and business advantages relative to batch methods. In general, continuous manufacturing methods are more robust and controllable. They achieve the same production rates as batch processes in much smaller and thus less capital-intensive equipment, which also requires less space to operate. They also facilitate automation that can be used to achieve significant improvements in product quality and process reliability. By combining impregnation and continuous manufacturing, the disclosed method achieves benefits afforded by both technologies and may be used as a rapid development platform to prepare clinical supplies and to introduce new drugs to market, or to manufacture those products at higher qualities and lower cost.

Further, the disclosed method(s) allow for an integrated technology for continuous impregnation that is designed and optimized based on a deeper understanding of the main components of the manufacturing system, helping to promote adoption of modern methodologies across an essential industry that at the present time often uses empirical methods and batch processes as its main development and manufacturing paradigm. The continuous manufacturing processes described herein may include sensing and control capabilities, such that the process is continuously monitored by various sensors and controllers to maintain the continuous process and the resulting products within the desirable operating range of process parameters and product quality attributes. Measurements collected from sensors can be used in conjunction with controllers and actuators arranged in a closed loop system (under closed loop control), using feedback, feed forward, and other configurations to control the performance of the process and the quality of the manufactured products.

The disclosed method also provides one or more significant advantages that make it very useful as a commercial method for drug product development and manufacturing. For example, the method is seemingly easy to perform, whereby a finished drug product may be made by spraying a solution or suspension of one or more drugs (typically produced during drug synthesis) onto a pre-formed porous carrier, drying the sprayed carrier, and, after optionally combining it with other ingredients known in the art, compacting it into tablets or filling it into capsules, vials, blister packs, or the like. This process can eliminate expensive processing steps, such as crystallization, drying, and milling of the drug material, batch blending with excipients, dry or wet granulation, drying or wet sizing of the granulation, sizing of the dry granulation, mixing the granulation with extragranular ingredients, blend lubrication, etc. By simplifying the process, the method significantly accelerates product development, reduces manufacturing cost, and precludes risk factors.

As disclosed herein, pharmaceutical drug products, such as solid oral dosage form pharmaceutical compositions, are suitable for administration to a subject, such as a human or other mammal. Non-limiting examples of solid oral dosage forms include tablets, capsules containing the impregnated carrier possibly together with other ingredients, capsules comprising a plurality of mini-tablets, powders, and granulations. Non-limiting examples of tablets include sublingual molded tablets, buccal molded tablets, sintered tablets, compressed tablets, chewable tablets, freeze-dried tablets, soluble effervescent tablets, and implants or pellets. Non-limiting examples of capsules, in which a solid dosage form of the drug is enclosed within a hard or soft soluble container or shell, include hard gelatin capsules, soft gelatin capsules, and non-gelatin capsules. In some embodiments, the finished solid oral dosage form may be modified to achieve a desired timing of API release—e.g., a dosage form that provides immediate release, sustained release, controlled release, extended release, partial immediate and partial delayed release, and combinations thereof.

The disclosed methods can also be used in the manufacture of non-oral products where a mixture of APIs and other solid ingredients is useful, including but not limited to the manufacture of inhalants, implantable and injectable solid compositions, vascular stents, and the like. While other types of porous materials might be needed in the formulation of such products, the inventive concepts disclosed here can be used in combination with routine experiments to implement methods and processes applicable to such products.

The disclosed methods, if properly implemented and aided by routine experiments varying process parameters such as spray rate, impeller rates, fluid temperatures, etc., can and will achieve a highly a uniform product (i.e., having a composition coefficient of variability below 1%) for blends containing any amount of drug from 0.1 wt % to 10 wt % or 0.5 wt % to 5 wt %. This is not known to be achieved by conventional dry processing methods where the product typically becomes less uniform (i.e., characterized by a higher RSD when sampled using unit dosage sampling) when the API content becomes smaller.

The disclosed method can also eliminate several expensive excipients from the formulation, thus further lowering cost and eliminating sources of variability that often cause quality problems in finished products.

The flow properties, compaction properties, and particle size distribution of an API-impregnated porous carrier made by the disclosed process are very similar to those of an unloaded carrier, and are largely independent of the API used in the process, thus providing an extremely useful platform for product development that works well for many different drugs. Consequently, API having poor or undesirable flow and compaction properties may be impregnated into a porous carrier having improved, desirable or advantageous flow and compaction properties using the continuous manufacturing process disclosed herein, thereby producing API-impregnated particles having predictable properties that are the same or very similar to those of the unimpregnated porous carrier particles. As a result, the disclosed method can produce API-impregnated carriers having excellent flow properties, relatively high bulk density (e.g., higher than 0.5 g/ml), excellent compressibility, and/or minimum tendency to acquire electrostatic charge, mainly by selecting a porous carrier with such properties and then impregnating the API onto that carrier. The disclosed method is also readily up- or down-scalable, facilitating manufacturing at both clinical trial and commercial scales and enabling rapid scale-up (or scale-down) and scale-out of manufacturing rates to meet changing market demands. In its simplest form, a continuous process enables the operator to make as much, or as little product as desired simply by changing the length of time the process is operated.

In one embodiment, the disclosed method includes impregnation of an API into a porous carrier in a fluidized bed using one or more transport solvents. Performing the impregnation in the fluidized bed avoids several challenges that may be encountered in other impregnation methods and/or traditional physical blends, and yields a product with significantly improved drug dissolution and blend uniformity, which are highly advantageous factors when developing and formulating APIs into various pharmaceutical dosage forms.

In general, impregnation is the process of placing chemical substances (such as drugs or APIs) inside porous carriers using a solution or a suspension that penetrates the pores of the carrier. While not willing to be bound by theory, it is commonly observed that penetration of the solution or the suspension is aided by capillary action, so that favorable wetting conditions and lower solution/suspension viscosity leads to faster impregnation. The high surface area of porous carriers allows them to absorb several compounds, including poorly flowing materials such as cohesive drugs. Since at the end of the process these compounds are completely (or nearly completely) embedded within the porous carriers, the flow and compaction properties of the impregnated products are very similar to the carrier, thereby facilitating their handling and further processing. While the bulk density of the impregnated carrier will often be higher than that of the original porous carrier, obeying to the partial or complete filling of pores with API and other substances, this change in density usually does not affect the performance of the impregnated carrier in undesirable ways. Moreover, at least some of the drug within the pores of the carrier typically exists in an amorphous form, which improve its dissolution.

Drug in amorphous form are known in the art and often used for the purpose of improving drug dissolution. In some cases, such amorphous drugs are physically unstable and exhibit a change in crystalline form over time, which can also result in changes to dissolution over the product shelf life. Improving the physical stability of such drug substances by porous carrier impregnation enhances the stability of important drug product properties, such as dissolution behavior. While not willing to be bound by theory, it is believed that the small sizes of many of the pores of the carrier result in confining of the drug, which limits the drug's mobility and its exposure to interstitial moisture, and also inhibits the drug's recrystallization inside the pores. Accordingly, impregnation into a porous carrier can improve crucial properties of the drug. Further, the disclosed process applies to impregnation using not only different APIs but also different porous carriers having different pore sizes, and the use of additional materials for the purpose of modulating drug dissolution, improving chemical and physical stability, and other desired features known to the skilled artisan.

In some embodiments, the selected solubilized crystalline API is applied to a porous carrier (e.g., sprayed into a fluidized bed of porous carrier), and then the solvent is removed, resulting in dried API-impregnated porous carrier with pores that are substantially filled with API. The API-impregnated porous carrier may then be solubilized, causing API to flow out from the pores and dissolve in the solvent.

Impregnation using an API solution or suspension as described herein renders unnecessary the finishing of the API crystallization, particle size optimization, and several additional API processing steps, thus greatly simplifying API manufacturing and substantially reducing the amount of effort, cost, and time required to produce drug products. API impregnation also eliminates other API processing challenges, such as API agglomeration, electrostatic charge development, API sticking to equipment, problems due to shear sensitive APIs, and change of API morphology or polymorphism during processing.

An example of a process for impregnating API solution throughout the volume of a porous carrier is described in U.S. Pat. No. 10,004,682, which is hereby incorporated by reference. In one embodiment of the presently disclosed process for preparing an API-impregnated porous carrier, a drug solution or suspension is impregnated throughout the volume of a porous carrier by spraying the solution/suspension onto the carrier in a fluid bed processor. The solvent is subsequently evaporated, providing a highly uniform composite particle of the carrier and the drug(s). The liquid medium used to create the solution/suspension (i.e., the solvent) is chosen to have high vapor pressure and low surface tension on porous carrier surfaces. Upon contact, capillary forces drive the solution/suspension into the porous carrier. Since the drug is deposited on the internal surface of the carrier, the external surface properties of the carrier remain largely unchanged regardless of the concentration of drug, or even the type of drug deposited. The API-impregnated porous carrier may be dried using a fluidized bed dryer, although other dryers can also be used. Optionally, the dried API-impregnated porous carrier can be subsequently milled to further improve uniformity. In some embodiments, the product may then be formulated into a finished solid oral dosage form—e.g., filled into capsules, vials, aerosol blisters, or compressed into tablets, after optionally mixing it with other ingredients known in the art.

In preparing the finished solid oral dosage form, API-impregnated porous carriers comprising one or more different APIs optionally may be blended with one or more pharmaceutically acceptable excipients. Non-limiting examples of such excipients include: carriers, such as cellulose or substituted cellulose materials, sodium citrate or dicalcium phosphate; fillers or extenders, such as starch-based materials, microcrystalline cellulose, lactose, sucrose, glucose, mannitol, and/or silicic acid; binders, such as hydroxypropyl cellulose, hydroxypropyl methylcellulose, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; absorption accelerators, such as quaternary ammonium compounds and surfactants, such as poloxamer and sodium lauryl sulfate; wetting agents, such as cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, zinc stearate, sodium stearate, stearic acid, and mixtures thereof; coloring agents; controlled release agents, such as crospovidone, ethyl cellulose, poly(ethylene oxide), alkyl-substituted celluloses, crosslinked polyacrylic acids, xanthan gum, guar gum, carrageenan gum, locust bean gum, gellan gum, methyl cellulose, hydroxypropyl methyl cellulose, hydroxyethyl cellulose, ethyl cellulose, sodium carboxymethyl cellulose, sodium alginate, gelatin, modified starches, co-polymers of carboxyvinyl polymers, co-polymer of acrylates, co-polymers of oxyethylene and oxypropylene and mixtures thereof; and other additives, such as paraffin and high molecular weight polyethylene glycols. In mentioning these materials, the use of the term "such us" means that the mentioned materials are simply examples belonging to a more extensive class. Also, as it is known in the art, most pharmaceutical ingredients have more than one useful function, and the mention of any one ingredient in any one of the above examples is not meant to exclude the use of that material for a different purpose. For example, starch can be a filler, a binder, and a disintegrant, and many other materials can also be used in more than one way.

In some embodiments, the disclosed technology relates to processes of continuously manufacturing a finished pharmaceutical drug product using an API-impregnated porous carrier made by either a continuous or a non-continuous (e.g., batch) process. In such embodiments, the material being processed in the continuous process flows through multiple simultaneous unit operations, including feeding API-impregnated porous carrier into feeder, optionally combining the API-impregnated porous carrier with one or more pharmaceutically acceptable excipients in a continuous blender, and compounding the mixture into a desired solid oral dosage form. Non-limiting examples of such formulating steps include filling the mixture into capsules, vials, or aerosol blisters, or compressing the mixture into tablets. In some embodiments of the process of formulating finished drug products, the API-impregnated porous carrier may exit a feeder (and, e.g., enter a blender) at a feed rate of up to 200 kg/h, such as 1 kg/h to 200 kg/h, 5 kg/h to 175 kg/h, 10 kg/h to 150 kg/h, 20 kg/h to 125 kg/h, or 2 kg/h to 100 kg/h. In some embodiments, the API-impregnated porous carrier displays a reduced tendency to stick to the equipment (e.g., the feeder) compared to non-impregnated API blended with porous carrier. For example, in some embodiments, less than 200 g, less than 150 g, less than 100 g, less than 50 g, less than 10 g, less than 5 g, 1 g to 175 g, or 10 g to 125 g of API-impregnated porous carrier may remain in a feeder after the feeder is allowed to discharge without refilling until no more API-impregnated porous carrier is discharged.

Impregnated carriers display many other advantageous properties. For example, such materials tend to be "free flowing," such that they will flow freely through an aperture with a diameter of about 1 inch, about 2 inches, or more. For further example, impregnated carriers might display a much smaller acquisition of electrostatic charge than the non-impregnated API when flowing through a gravimetric feeder, as measured by a Faraday cage method. Additionally, API-impregnated carriers will show a much smaller tendency to densify than the non-impregnated API when flowing through a gravimetric feeder, as measured using a bulk density method. Moreover, API-impregnated carriers will show a much smaller tendency to agglomerate (e.g., wherein API particles impregnated into different carriers adhere together) than the non-impregnated API when flowing through a gravimetric feeder, as measured by a suitable particle size analysis method or, alternatively, as evidenced in the content uniformity of the finished product.

In general, the API impregnation process includes the steps of: dissolving or suspending at least one API in a solvent to form an API solution or a suspension; contacting a porous carrier with the API solution or suspension in a contactor to form an API-impregnated porous carrier; and drying the API-impregnated porous carrier, wherein any single API content variability in the dried API-impregnated porous carrier powder has a relative standard deviation (RSD) of less than 3% when RSD is determined from a sample of at least 200 mg of API-impregnated porous carrier powder, or any other sample size containing up to three times the amount of API-impregnated carrier as it might be intended to be used in a single unit dose of finished product.

Throughout this patent, the reference to an "API suspension" refers to a suspension of undissolved API particles in a suitable volatile fluid that may be used to impregnate such particles into the carrier pores. While not wishing to be bound by a particular theory, it is a reasonable principle that in order to be able to be impregnated, such undissolved particles should be of a mass-based average size significantly smaller, i.e., at least 10 times smaller, than the mean pore size of the porous carrier.

The API solution spray rate is calculated as the mass of the API solution or suspension being sprayed (kg) divided by the product of the total spray time (s) and the mass of the carrier (kg). In some embodiments of the disclosed continuous manufacturing process, the API solution spray rate is less than 1 s$^{-1}$, less than 0.5 s$^{-1}$, less than 0.4 s$^{-1}$, less than 0.3 s$^{-1}$, less than 0.1 s$^{-1}$, or in the range of 0.01 s$^{-1}$ to 1 s$^{-1}$, 0.01 s$^{-1}$ to 0.5 s$^{-1}$, 0.05 s$^{-1}$ to 0.5 s$^{-1}$, 0.1 s$^{-1}$ to 0.5 s$^{-1}$, 0.01 s$^{-1}$ to 0.4 s$^{-1}$, 0.05 s$^{-1}$ to 0.4 s$^{-1}$, or 0.1 s$^{-1}$ to 0.4 s$^{-1}$.

In a process of forming the API-impregnated porous carrier, the solvent may be an inorganic or organic liquid. Non-limiting examples of suitable liquids that may be used in the disclosed method include ethanol, methanol, isopropyl alcohol (IPA), acetone, 1-propanol, 1-pentanol, acetonitrile, butanol, methyl ethyl ketone (MEK), methyl acetate, 2-methyl tetrahydrofuran, isopropyl acetate (IPAc), n-hexane, ethyl acetate (EtOAc), n-heptane, water, an aqueous solvent, supercritical $CO_2$, and combinations thereof.

In some embodiments, the concentration of API in the solvent may be in the range of $10^{-6}$ wt to 40 wt %, $10^{-6}$ wt to 30 wt %, $10^{-6}$ wt to 20 wt %, $10^{-6}$ wt to 10 wt %, $10^{-6}$ wt to 1 wt %, $10^{-5}$ wt to 40 wt %, $10^{-5}$ wt to 30 wt %, $10^{-5}$ wt to 20 wt %, $10^{-5}$ wt to 10 wt %, $10^{-5}$ wt to 1 wt %, $10^{-4}$ wt to 40 wt %, $10^{-4}$ wt to 30 wt %, $10^{-4}$ wt to 20 wt %, $10^{-4}$ wt to 10 wt %, $10^{-4}$ wt to 1 wt %, $10^{-3}$ wt to 40 wt %, $10^{-3}$ wt to 30 wt %, $10^{-3}$ wt to 20 wt %, $10^{-3}$ wt to 10 wt %, $10^{-3}$ wt to 1 wt %, $10^{-2}$ wt to 40 wt %, $10^{-2}$ wt to 30 wt %, $10^{-2}$ wt to 20 wt %, $10^{-2}$ wt to 10 wt %, $10^{-2}$ wt to 1 wt %, 0.1 wt to 40 wt %, 0.1 wt to 30 wt %, 0.1 wt to 20 wt %, 0.1 wt to 10 wt %, 0.1 wt to 1 wt %, 1 wt to 40 wt 1 wt to 30 wt %, 1 wt to 20 wt %, 1 wt to 10 wt %, or 1 wt to 5 wt %. In all cases, "wt %" is calculated by dividing the amount of API in a sample or a batch by the total weight of the sample or the batch.

Non-limiting examples of suitable porous carriers include magnesium aluminum metasilicate, granulated silicon dioxide, dibasic calcium phosphate, calcium hydrogen phosphate ($CaHPO_4$), porous carriers identified in the Geldart classification, *Powder Technology*, 7:285-292 (1973) as Group A and/or Group B carriers, and combinations thereof. In some embodiments, the porosity of the carrier in terms of pores by volume may be 20% to 85%, 20% to 70%, 20% to 60%, 20% to 50%, 20% to 40%, 20% to 30%, 30% to 50%, 50% to 70% or 70% to 85%. In some embodiments, the average pore size of the porous carrier may be 100 nm to 2000 nm, 100 nm to 1500 nm, 100 nm to 1000 nm, 100 nm to 500 nm, 200 nm to 2000 nm, 200 nm to 1500 nm, 200 nm to 1000 nm, 200 nm to 500 nm, 300 nm to 2000 nm, 300 nm to 1500 nm, 300 nm to 1000 nm, or 300 nm to 500 nm. Average pore size may be determined by BET and other absorption-desorption methods, mercury intrusion porosimetry, scanning electron microscopy, image analysis, or any other suitable method. The porous carrier may be a pharmaceutically acceptable carrier that is appropriate for use in the intended finished dosage form.

In some embodiments, the API-impregnated porous carrier has substantially uniform distribution of one or more APIs, such that any single API content variability in a finished drug product has a relative standard deviation (RSD) of less than or equal to 2.5%, less than or equal to 2%, less than or equal to 1.5%, less than or equal to 1%, less than or equal to 0.5%, or less than or equal to 0.1%.

Any suitable, pharmaceutically suitable drug or pro-drug substance may be used in the disclosed method. One or more different APIs (e.g., 1, 2, 3 or more APIs) may be impregnated into the porous carrier. In some embodiments, multiple APIs may be dissolved in solution in a fixed ratio (e.g., 1:1 to 3:1, 2:1, and variations thereof), after which the multi-API solution may be sprayed into the porous carrier to achieve API-impregnated porous carrier having the same fixed ratio of APIs.

Specific APIs disclosed herein are provided for illustrative purposes only and do not limit the scope of the disclosed technology. In general, the API used in impregnation should possess three main properties: be stable under relevant experimental conditions, be soluble to a significant extent in different types of solvents, and be inert when combined with the porous carrier. In some embodiments, the API is suitably soluble in a volatile organic solvent. In some embodiments, the API is at least partially in amorphous form after impregnation. In some embodiments, the API is at least partially in crystalline form. In some embodiments, the API is suitably soluble in water, while in some other embodiments, the API is poorly soluble in water, e.g., the API solubility is less than 10 mg/ml. In yet other embodiments, the solubility of the API in water can be increased or decreased by modifying the pH of the solution. Yet in other embodiments, the pH-modifying substance is itself volatile (e.g., ammonia, $CO_2$, and other such substances) such that it modifies the solubility of the API (or other substances present) during impregnation, but is largely eliminated by evaporation during the drying step of the process. Some non-limiting examples of APIs include acetominophen, ibuprofen, indometacin/indomethacin, flufenamic acid, imatinib, flufenamic acid, erlotinib hydrochloride, vitamin D, steroids, estrodial, other non-steroidal anti-inflammatory drugs (NSAIDs), and combinations thereof.

The disclosed continuous impregnation process is usually maintained in a near-steady state motion. In order to get a successful continuous impregnation process, the time window for impregnation is much shorter in a continuous process than in a batch process. In a batch process, there is a set amount of API solution that is sprayed over time. In a continuous process, carrier powder constantly moves through the system. Therefore, the solution addition rate needs to be adjusted to the carrier flow rate to reach a desired output ratio of API-impregnated porous material. Hence, in the disclosed continuous impregnation process, it is important to adjust the spray rate according to the mean residence time and flow rate of carrier powder from the powder feeder. Also, it is important to determine the maximum allowed spray rate to avoid agglomeration of the porous carrier due to local excesses of solution. This step largely depends on the properties of the porous carrier and the throughput of the API material. Those skilled in the art would know how to determine appropriate conditions using routine experiments that examine the effect of varying the aforementioned flow rates. The disclosed continuous manufacturing process might include a series of unit operations and online testing equipment. In one embodiment, the process includes a first feeder (such as a loss-in-weight feeder), a continuous blender, an optional analytical instrument (such as a near infrared (NIR) spectroscopy instrument), a pump (such as a peristaltic or vacuum pump), and a second feeder (e.g., gravimetric, vibratory, etc.). The first feeder is used to accurately dispense porous carrier particles. From the feeder, the porous carrier particles flow directly into a continuous blender, where the porous carrier particles undergo tumbling. The API-impregnation step described above occurs in the continuous blender into which API solution is sprayed. API-impregnated carrier particles then flow (e.g., fall by gravity) from the continuous blender to a second, transitional feeder, which controls the bed height. An analytical instrument, such as a NIR probe, may be positioned above the transitional feeder to obtain spectral scans of the API-impregnated carrier particles passing underneath.

FIG. 1 shows an example of a portion of the disclosed continuous manufacturing process, wherein porous carrier is fed from a first feeder into a continuous blender into which API solution is sprayed in order to form particles of API-impregnated porous carrier. The first feeder accurately dispenses or meters the porous carrier particles into the continuous blender. In some embodiments, the first feeder is a loss-in-weight feeder. In some embodiments, the feed rate of the carrier from the first feeder is 1 kg/h to 200 kg/h, 2 kg/h to 150 kg/h, 3 kg/h to 100 kg/h, 5 kg/h to 90 kg/h, 10 kg/h to 80 kg/h, 20 kg/h to 50 kg/h, or 2 kg/h to 15 kg/h.

The continuous blender (e.g., tubular mixer, vertical continuous blender, zig zag mixer, etc.) may perform multiple operations within the continuous API impregnation process. In simple terms, impregnation includes two main steps: (1) mixing of API solution with a porous carrier, and (2) drying the resulting product. In the context of the disclosed process, agglomeration is undesirable and to be avoided, minimized or eliminated from the process. Agglomeration may occur when the spray rate is high such that a liquid layer of API solution exist around the host carrier, which "glues" the particles to each other. Agglomeration or granulation may also occur when the impregnation ratio is too high, which allows a high amount of API solution to penetrate the pores, leading to pore saturation, accumulation of API solution at the surface of carriers and (undesirable) granulation.

Impregnation is desirably achieved when Ri (impregnation rate)>Rd (drying rate)≥Rs (spray rate). This allows for both high penetration of API solution into the pores of the porous carrier and evaporation of solvent before saturation.

Figure 2:
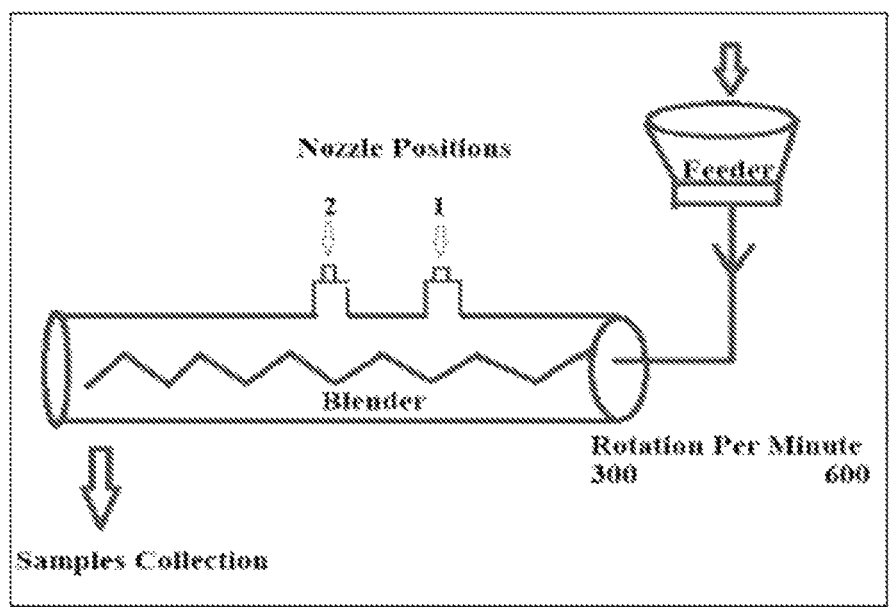
FIG. 2 shows an example schematic of a portion of the disclosed continuous manufacturing process for the impregnated carrier, wherein porous carrier enters a first feeder and is fed into a continuous blender that is supplied with two nozzles through which API solution/suspension is sprayed in order to form particles of API-impregnated porous carrier inside the blender, which are then collected on a vibratory feeder for continued processing.

FIG. 2 also shows an example of a portion of the disclosed continuous manufacturing process, wherein porous carrier is fed from a first feeder into a continuous blender and API solution is simultaneously sprayed into the continuous blender. The continuous blender is supplied with at least one nozzle (e.g., one, two, three, four, or more nozzles) for spraying of the API solution into the porous carrier. The nozzle(s) may be located at various positions along the axis of the blender, such as near the blender entrance (e.g., approximately 25% of the full length of the blender) and/or at or near the midpoint of the blender. API solution may be directed to the nozzle(s) via tubing, such as Tygon® (flexible polymer) tubing. One or more nozzles may have a diameter of 0.05 mm to 0.5 mm, 0.1 mm to 0.4 mm, or 0.2 mm to 0.3 mm. A pump, such as a peristaltic pump, may be utilized to deliver the API solution to the continuous blender—e.g., from a source supply of API solution through the tubing connected to the one or more nozzles, and then into the blender.

In some embodiments, the API solution is delivered into the continuous blender at a pump rate of up to 1000 ml/min, such as 1 ml/min to 1000 ml/min, 10 ml/min to 800 ml/min, 20 ml/min to 600 ml/min, 30 ml/min to 500 ml/min, 20 ml/min to 400 ml/min, 55 ml/min to 300 ml/min, 85 ml/min to 200 ml/min, 25 ml/min to 100 ml/min, or 60 ml/min to 90 ml/min. Ingredients in the continuous blender are mixed and impregnated simultaneously. The blender may be operated at various rotation speeds, such as 150-600 rpm, 150-300 rpm, 300-600 rpm, about 150 rpm, about 300 rpm, or about 600 rpm.

In some embodiments, the continuous blender is a continuous tubular blender. In some embodiments, the continuous blender includes multiple blades or paddles. For example, the blender may have a one-third forward-alternating-forward blade configuration, wherein a first set of paddles (e.g., 5-10 paddles or 6-8 paddles), an optionally equal last set of paddles are all angled in the forward direction to convey the powder forward through the process, and an optionally equal middle set of paddles may be angled in an alternating forward and backward direction, creating a zone of back-mixing. An alternating angle pattern of blades in the continuous blender can create a region of material hold-up, which may be a desirable region into which the API solution is sprayed in order to more effectively dispense the API solution across the porous carrier material.

API impregnation of the porous carrier occurs immediately once the carrier material reaches a nozzle-sprayed position inside the blender. The mean residence time (MRT) is the time spent by the API or a detectable tracer material inside the continuous blender during the disclosed continuous manufacturing process. In some embodiments, the MRT is about 1 min to about 30 min, about 3 min to about 20 min, about 4 min to about 16 min, about 8 min to about 10 min, about 1 min to about 3 min, about 1 min to about 5 min, about 1 min to about 7 min, or about 1 min to about 10 min.

Figure 3:
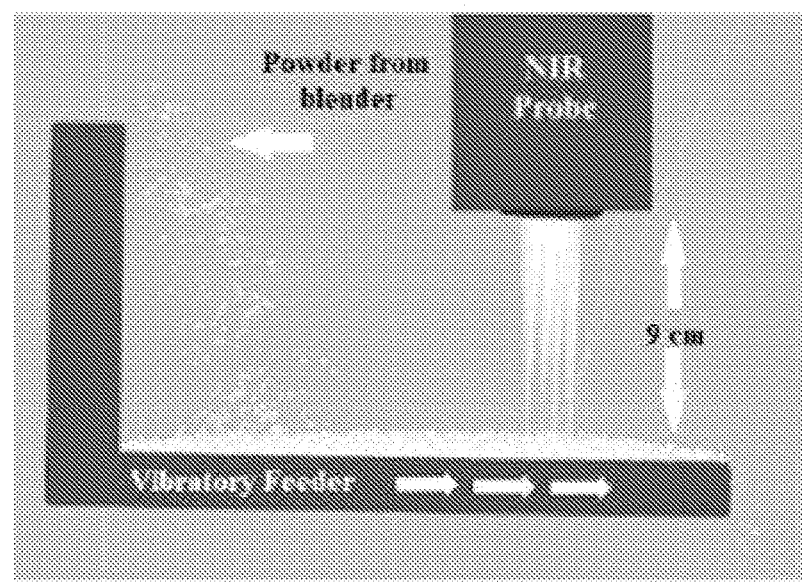
FIG. 3 shows an example schematic of a portion of the disclosed continuous manufacturing process for finished dosage forms, wherein powder particles of API-impregnated porous carrier flow from a continuous blender onto a gravimetric feeder (in this case, without limitation, a gravimetric vibratory feeder) and pass under a near infrared (NIR) probe. The measurement from the probe can be used, in conjunction with a controller and an actuator, to maintain the process at desired conditions.

FIG. 3 shows an example of another portion of the disclosed continuous manufacturing process, wherein powder particles of API-impregnated porous carrier flow from the continuous blender to a vibratory feeder, which conveys the powder under a NIR probe. In other embodiments, a different and/or additional analytical device may be utilized to monitor the status of the powder on the vibratory feeder.

After impregnation, API-impregnated porous carrier is collected from the continuous blender and dried using a fluidized bed (e.g., a Glatt fluidized bed dryer or equivalent thereof) in order to remove residual solvent. In the fluidized bed dryer, the temperature of inlet air may be 70° C. to 90° C., such as about 80° C. In the fluidized bed dryer, the air flow pressure may be 0.05 bar to 0.3 bar, or 0.1 bar to 0.15 bar. Other types of continuous dryers, such as a belt dryer, or a heated screw conveyor, or a heated twin screw processor, might also be used instead of the fluidized bed dryer for the purpose of removing the solvent and drying the API-impregnated carrier.

After the impregnation and drying steps occurs in the continuous blender and dryer, the resulting API-impregnated powder may be deposited onto a second feeder (e.g., gravimetric, vibratory, etc.), to control its flow into downstream processing units, and optionally an analytical device such as an NIR probe may be utilized to scan the powder bed and determine composition and residual solvent content. Such a measurement can be used in conjunction with a controller system to adjust the API solution spray ratio and the dryer temperature, so that API composition and residual solvent content of the API-impregnated carrier can be controlled. In general, the second feeder transports or conveys the impregnated products continuously without interfering with flowability.

From the second feeder, the API-impregnated porous carrier may be formulated into a finished drug product. Non-limiting examples of finished drug products include solid oral dosage forms such as tablets, capsules, powders, and granulates. The finished drug product may be further provided in appropriate packaging, such as but not limited to a blister pack, or vial.

Dissolution testing may be performed to determine the release drug profile of the API-impregnated carrier and also of finished dosage forms manufactured using the API-impregnated carrier. Among various devices suitable for dissolution testing known to someone of skill in the art, a 708-DS, 8-spindle, 8-vessel USP dissolution apparatus type II (paddle), with automated online UV-Vis measurement (Agilent Technologies) might be used for such measurements. As previously described, different carriers, and additional ingredients such as control release polymers, can be used to impart the API-impregnated carrier, and the products compounded from them, with any desired drug release profile, including, without limitation:

An immediate release profile, where either the API-impregnated carrier or the finished drug product manufactured using the API-impregnated carrier releases at least 80% of the API in less than 45 minutes, at least 80% of the API in less than 30 minutes, at least 80% of the API in less than 15 minutes, at least 80% of the API in less than 10 minutes, when tested in a USP II apparatus using simulated gastric fluid with pH<2, 50 RPM, and 37° C.

An immediate release profile, where either the API-impregnated carrier or the finished drug product manufactured using the API-impregnated carrier releases at least 80% of the API in less than 45 minutes, at least 80% of the API in less than 30 minutes, at least 80% of the API in less than 15 minutes, at least 80% of the API in less than 10 minutes, when tested in a USP II apparatus using de-ionized water, 50 RPM, and 37° C.

A sustained release profile, where either the API-impregnated carrier or the finished drug product manufactured using the API-impregnated carrier releases less than 80% of the API after 60 minutes, or after 120 minutes, or after 240 minutes, or after 360 minutes, or after 480 minutes, or after 1440 minutes, when tested in a USP II apparatus using de-ionized water, 50 RPM, and 37° C.

A sustained release profile, where either the API-impregnated carrier or the finished drug product manufactured using the API-impregnated carrier releases less than 80% of the API after 60 minutes, or after 120 minutes, or after 240 minutes, or after 360 minutes, or after 480 minutes, or after 1440 minutes, when tested in a USP II apparatus using pH=6.8 buffer, 50 RPM, and 37° C.

A delayed release profile, where less than 5% of the API, or less than 10% of the API, is released after one hour, when tested in a USP II apparatus using simulated gastric fluid with pH<2, 50 RPM, and 37° C. A pulsated profile, obtained by combining two or more fractions of API-impregnated carriers having different particle sizes and/or different pore sizes, and/or optionally containing different amounts of controlled release agents.

Other release profiles that represent combinations of the previously described release profiles, that might be obtained by a combination of the inventive concepts disclosed herein and non-inventive routine experimentation.

EXAMPLES

The disclosed technology is next described by means of the following non-limiting examples. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled. Efforts have been made to ensure accuracy with respect to values presented (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

This example describes one embodiment of the disclosed continuous processing for manufacturing pharmaceuticals using continuous impregnation of API onto porous carriers. Two host porous carriers were used in this study: dibasic calcium phosphate (FUJICALIN®) and magnesium aluminometasilicate (NEUSILIN® US2) obtained from Fuji Chemical Industries Co., Ltd. (Japan). The API used in this study was Ibuprofen 70 (IBU). Ibuprofen was the API used for impregnation and as a liquid phase tracer in residence time distribution (RTD) measurement. Analytical grade methanol was used as the transport solution, to dissolve the Ibuprofen, and pump it into the devices. The continuous impregnation process included multiple unit operations and online testing equipment including a loss-in-weight (LIW) feeder, a continuous blender, a near infrared (NIR) spectroscopy instrument, a peristaltic pump, and a vibratory feeder. The equipment used in this study included a Glatt continuous powder blender (GCG-70), a single K-Tron K-CL-SFS KT20 (Coperion K-Tron Pitman Inc., NJ) feeder for manufacturing of impregnated products, and a FT-NIR Matrix (Bruker Optics Billerica, MA, USA) for spectral acquisition to study RTD and RSD of impregnated products.

First, porous carrier was fed through the LIW feeder into the blender, where the impregnation step occurred immediately once the material reached the nozzle position inside the blender. A peristaltic pump was used to deliver the drug solution through tubing connected to the 0.1 mm diameter nozzle. See FIGS. 1-2. Next, the impregnated products were dried using a Glatt fluidized bed to exclude any residual solvent. The temperature of inlet air was 80° C. The air flow pressure was 0.10-0.15 bar. Once dried, particle size was characterized using a Beckman-Coulter LS 13-320, with a Tornado module for dry powder.

Residence Time Distribution (RTD) Measurement

Residence time distribution in the blender was calculated to determine the RTD of the API in the liquid phase. The API (ibuprofen) was used as the tracer as it has a clear and distinguishable NIR peak. To calculate the RTD of tracers in liquid phase (ibuprofen in methanol), the continuous process was first allowed to reach steady state by monitoring the exit flow rate of the system. This was done by allowing the porous carrier (dibasic calcium phosphate or magnesium aluminometasilicate) to be fed into the blender for 10-15 min. Once steady state was achieved, the tracer was added, and the time of the pulse was noted. These experiments were performed at 150 and 300 rpm and using a 3 kg/h feed rate. The amounts of tracer were selected such that the concentration of the tracer at the exit of the blender would be detectable by the NIR method.

The ibuprofen solution, used as the liquid form tracer, was prepared by dissolving ibuprofen into methanol to obtain a 20% w/w ibuprofen in methanol solution. The solution was then added into the system using a peristaltic pump at 3 different speeds (25, 60, and 90 rpm). The pump was run for 1 minute for each condition. NIR spectra were subsequently acquired at constant time intervals from the outlet of the mixer. These spectra were analyzed to determine the concentration of tracers over time. Thus, a dataset of concentration vs. time was collected.

RSD Measurement

To evaluate the quality of mixing (mixing performance) over time, the relative standard deviation of the API content in the impregnated product was computed. Once the powder flow reached a steady state, the drug solution was constantly pumped into the blender and allowed to reach the steady state. When the steady state was achieved by observing constant NIR readings, 100 spectra were collected over the course of the run. The average API concentration was calculated along with the standard deviation. The RSD was then calculated as the ratio of the standard deviation over the average.

To measure the content homogeneity of the carrier exiting the blender, four impregnation experiments were run using the two carriers in this study, and blender speeds of 150 and 300 rpm. The API solution pump rate was 25 ml/min and the porous carrier feeding rate was 3 kg/hr. At the beginning, the carrier materials were fed until reaching the steady state by monitoring weight versus time exiting the blender. Then, the API solution was pumped for a while to reach the steady state. After that, 100 NIR spectra were collected for each experiment and analyzed to calculate the RSD. The RSD results are shown in Table 1, wherein "Actual Loading" refers to grams of ibuprofen in 50 grams of carrier.

TABLE 1

| Porous Carrier | RPM | Actual Loading | % RSD |
|---|---|---|---|
| Magnesium Aluminometasilicate | 150 | 5.01 | 1.89 |
| | 300 | 5.59 | 1.11 |
| Dibasic Calcium Phosphate | 150 | 5.15 | 2.28 |
| | 300 | 5.4 | 2.51 |

In all cases, the RSD % values were very low (less than or equal to 2.5%), which indicates that the API-impregnated porous carriers prepared by the continuous manufacturing process disclosed herein exhibit surprisingly excellent homogeneity.

Example 2

This example describes another embodiment of the disclosed continuous processing for manufacturing pharmaceuticals using continuous impregnation of API onto porous carriers. The host porous carrier used in this study was dibasic calcium phosphate (FUJICALIN®) obtained from Fuji Chemical Industries Co., Ltd. (Japan). The API used in this study was Ibuprofen 70 (IBU). Ibuprofen was the API used for impregnation and as a liquid phase tracer. Analytical grade methanol was used as the transport solution, to dissolve the Ibuprofen, and pump it into the devices. The API solution was prepared by dissolving 100 g ibuprofen (amorphous) in 1500 g methanol.

A Glatt continuous blender (GCG-70) with a granulation shaft was used to impregnate IBU into the porous carrier. The experimental conditions included: pump rate of 25 ml/min; powder feeding rate of 5 kg/h; and blender speed of 300 rpm or 600 rpm. The blender included two nozzles: a first nozzle was located at a first position, 25% of the distance along the longitudinal axis of the blender as measured from the entrance; and a second nozzle was located at a second position, at the middle point along the longitudinal axis of the blender. A peristaltic pump was used to deliver the drug solution through tubing connected to the nozzles. See FIG. 2. Next, the impregnated products were dried using a fluidized bed at elevated temperature and air flow pressure to remove residual solvent. Once dried, particle size was characterized in a similar manner to Example 1.

Mean Residence Time

The mean residence time (MRT) of the continuous blender was determined using an independent measurement of the powder hold-up. The impregnated products were analyzed by UV-spectroscopy to measure average loading and blend uniformity of the impregnated IBU. Physico-chemical characterization was conducted using a Laser-diffraction, Scanning Electron Microscopy, FT4 (shear cell), Raman spectroscopy, XR-ray diffraction and dissolution behavior. MRT was calculated from blender hold up using the following formula:

$$\text{Mean Residence Time (h)} = \frac{\text{Mass Hold-Up (kg)}}{\text{Feeding Rate}\left(\frac{\text{kg}}{\text{h}}\right)}$$

MRT was calculated to be 178 seconds at 300 rpm, and 47 seconds at 600 rpm. The results showed that the rotation speed affected both the blender hold-up and the MRT. After increasing the rotation speed from 300 rpm to 600 rpm, the MRT is reduced from 178 sec to 47 sec. This is due to the decrease in the powder hold-up, and consequently in the value of MRT, as the rotation speed of the blender increases.

The Raman spectroscopy results showed that IBU mainly existed in amorphous state. The pure IBU exhibited sharp peaks in the regions between (1200-1800 cm-1) while these peaks disappeared in the IBU impregnated products. The absence of these sharp peaks from impregnated products indicated that the IBU existed in amorphous form in these products.

RSD Measurement

To evaluate the quality of mixing (mixing performance) over time, the relative standard deviation of the API content in the impregnated product was computed. Once the powder flow reached a steady state, the drug solution was constantly pumped into the blender and allowed to reach the steady state. When the drug solution steady state was achieved by observing constant NIR readings, spectra were collected over the course of the run. The average API concentration was calculated along with the standard deviation. The RSD was then calculated as the ratio of the standard deviation over the average.

Initially, the carrier materials were fed until reaching a steady state by monitoring weight versus time exiting the blender. Then, the API solution was pumped for a while to reach the steady state. After that, NIR spectra were collected for each experiment and analyzed to calculate the RSD. The RSD results are shown in Table 2.

TABLE 2

| Nozzle Position | Blender RPM | % Loading | % RSD |
|---|---|---|---|
| 1 | 300 | 1.82 | 3.1 |
| | 600 | 1.81 | 3.4 |
| 2 | 300 | 1.49 | 4.7 |
| | 600 | 1.43 | 2.3 |

In all cases, the % RSD values were low, which indicates that the API-impregnated porous carriers prepared by the continuous manufacturing process disclosed herein exhibit surprisingly excellent homogeneity.

Figure 4:
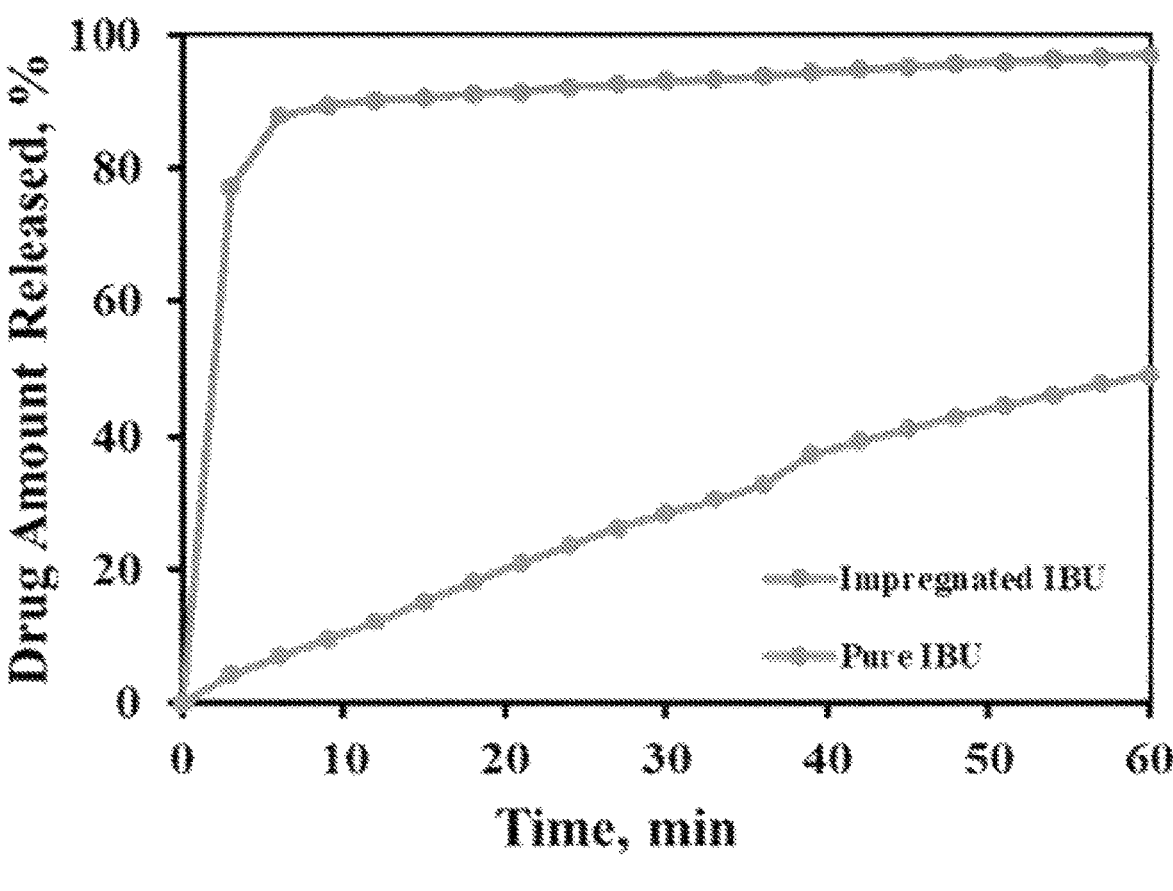
FIG. 4 shows a comparison of dissolution profiles for IBU tablets made from a dry blend of the API and the carrier, and tablets made from the IBU-impregnated carrier, as described in Example 2.

Dissolution Behavior: As part of this study, dissolution tests were performed on both pure IBU and impregnated IBU to check the effect of the impregnation process on the dissolution rate and extent of IBU. Dissolution was carried out in 900 ml of DI water at 50 rpm and 37° C. using the rotating paddle method. Samples were withdrawn at predetermined time intervals (every 3 minutes) for 60 min using a peristaltic pump attached to the dissolution device. The amount of released IBU was quantified spectrophotometrically. The results presented in FIG. 4 demonstrated that the impregnated product releases about 85% of IBU within less 5 minutes while less than about 10% of pure crystal IBU was released within 5 minutes. Hence, when rapid dissolution of a poorly soluble drug is desirable, a continuous manufacturing process using API-impregnated porous carriers as disclosed herein provides a highly efficient and advantageous technique.

Particle Size Distribution (PSD): $D_{10}$, $D_{50}$, and $D_{90}$ PSD of the pure Fujicalin (FUJ) and 2% IBU-FUJ impregnated product using high shear blender at 600 rpm were measured. As shown below in Table 3, impregnation of IBU at 600 rpm had an impact on $D_{10}$, $D_{50}$, and $D_{90}$ as compared with pure FUJ before impregnation. Mixing speed at 600 rpm resulted in a decrease of $D_{10}$ from 63 μm to 32.6 μm, D50 from 131 μm to 111.6 μm and $D_{90}$ from 180 μm to 146 μm. Without being bound by a particular theory, the data suggest that this process was associated with a particle size reduction due to high shear attrition of the carrier by the blender blades. Thus, PSD of the impregnated product shifted toward small particle size.

TABLE 3

| Product | $D_{10}$ (μm) | $D_{50}$ (μm) | $D_{90}$ (μm) |
|---|---|---|---|
| Pure FUJ | 63 | 131 | 180 |
| 2% IBU-FUJ | 32.6 | 111.6 | 146 |

Example 3

This example describes a study comparing the properties of two formulations made from the same materials, wherein one composition was prepared by blending the API and carrier in dry form, and the other composition was prepared by impregnating the API into the carrier.

Direct Compression (DC) Tablets were prepared by a continuous manufacturing process, in which porous carrier and API were blended together in a continuous blender to form a powder that was then subjected to direction compression to produce tablets. In preparing the DC Tablets, API and porous carrier were combined in dry form without the use of solvents, but the API was not sprayed into a fluidized bed of porous carrier.

Impregnated Tablets were prepared by a continuous manufacturing process, in which API was dissolved in a solution that was sprayed into a continuous blender containing porous carrier so as to form API-impregnated porous carrier powder in accordance with the methods for continuous manufacturing of pharmaceuticals by continuous impregnation onto porous carriers disclosed herein.

For all tablets prepared in this study, the API was ibuprofen, the porous carrier was magnesium aluminometasilicate (NEUSILIN®), and the continuous blender was a Glatt continuous powder blender (GCG-70). The compositions of the DC Tablets and Impregnated Tablets are shown below in Table 4.

TABLE 4

| Component | DC Tablet | Impregnated Tablet |
|---|---|---|
| Ibuprofen (IBU) | 4 wt % | — |
| PROSOLV ® (silicified microcrystalline cellulose) | 69 wt % | 69 wt % |
| NEUSILIN ® (NEU) (magnesium aluminometasilicate) | 26 wt % | — |
| 13% IBU-NEU impregnated product | — | 30 wt % |
| magnesium stearate | 1 wt % | 1 wt % |
| Total | 100 wt % | 100 wt % |

Samples of powder were collected from both the direct compacted blend and the impregnated blend after the blender and before the feed frame. Samples of both types of finished tablets (DC Tablet and Impregnated Tablet) were also collected. All samples were assayed for blend uniformity, content uniformity, and dissolution behavior.

Blend Uniformity: A specified amount of 12 samples were placed in methanol. The samples were then sonicated for 50 min and left overnight. UV spectra were acquired at 265 nm for all samples.

Content Uniformity: 12 tablets were individually crushed using mortar and pestle. The resulting powder was placed in methanol. The samples were then sonicated for 50 min and left overnight. UV spectra were acquired at 265 nm for all samples.

The results of the assays determining blend uniformity and content uniformity of the powder and tablet samples are provided in Table 5 below.

TABLE 5

| Sample | IBU (wt %) | % RSD |
|---|---|---|
| IBU-NEU Impregnated Carrier | 13.78 | 2.73 |
| Impregnated Blend (before Feed Frame) | 4.87 | 2.68 |
| Impregnated Tablet | 4.36 | 2.45 |
| Direct Compaction Blend (before Feed Frame) | 4.6 | 5.27 |
| Direct Compaction Tablet | 4 | 4.42 |

The Impregnated Tablets demonstrated unexpectedly and substantially superior homogeneity as compared to the DC Tablets.

Dissolution Behavior: Assessments of dissolution behavior were conducted on 5 Impregnated Tablets and 5 DC Tablets under the following conditions:

Medium: HC1 solution (pH 1.8) without surfactants.
RPM: 50
Apparatus II (Paddle)
Interval: 5 min
Duration: 75 min
Detection: Ultraviolet Spectroscopy at 220 nm
Temperature: 36° C.

Figure 5:
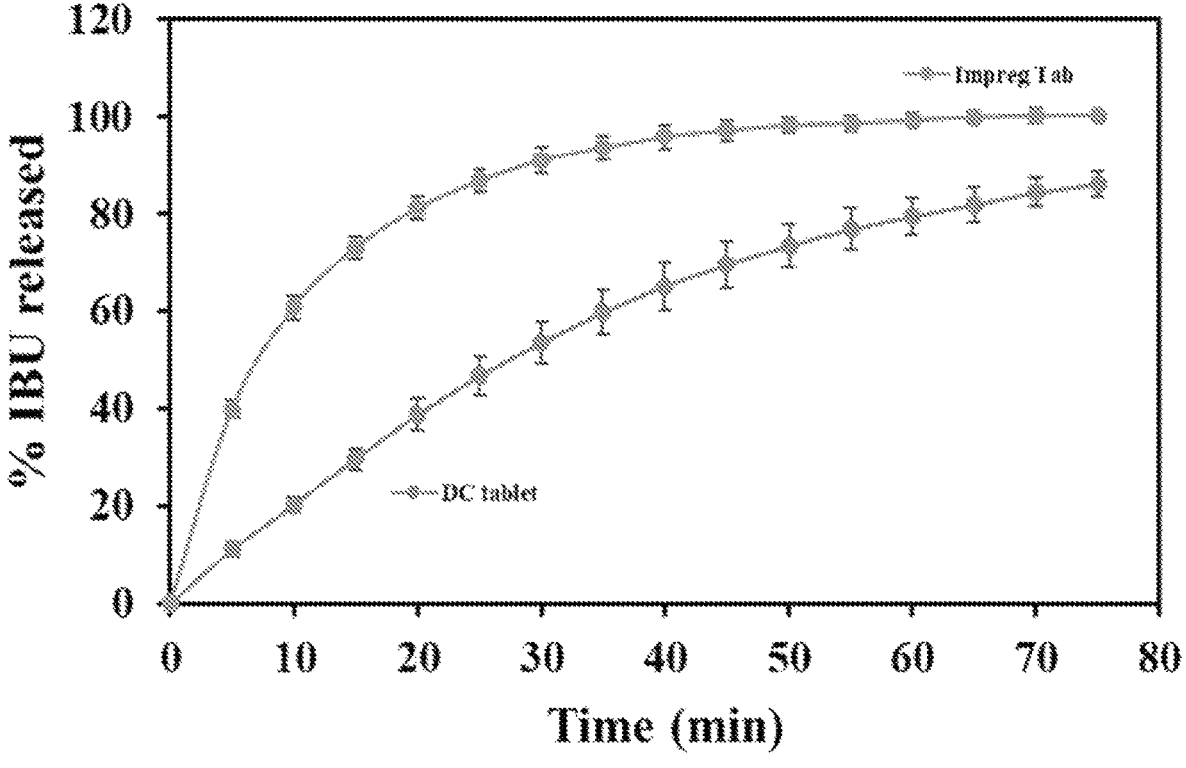
FIG. 5 shows a comparison of dissolution profiles for tablets made from impregnated carrier, and tablets made by direct compression of a physical blend of the IBU and the carrier, as described in Example 3.

The results of this dissolution testing are shown in FIG. 5, and show that the Impregnated Tablets surprisingly released far more API at a substantially faster rate than the DC Tablets. For example, the Impregnated Tablets released more than 50% of the API in less than 10 minutes, whereas it took more than 20 minutes for the DC Tablets to release more than 50% of the API. Also, the Impregnated Tablets released about 80% API in about 20 minutes, whereas it took more than 60 minutes for the DC Tablets to release the same amount. Hence, when rapid dissolution of a poorly soluble drug is desirable, the dissolution behavior of pharmaceutical compositions made by a continuous manufacturing process using API-impregnated porous carriers is highly advantageous.

The foregoing merely illustrates the principles of the disclosure. Any examples set forth in this specification are not intended to be limiting and merely set forth some of the many possible embodiments for the appended claims. Those skilled in the art will readily recognize various modifications and changes that may be made without following the example embodiments and applications illustrated and described herein, and without departing from the true spirit and scope of the following claims.

All references cited and/or discussed in this specification are incorporated herein by reference in their entireties and to the same extent as if each reference was individually incorporated by reference.

We claim:

1. A continuous flow process for manufacturing API-impregnated porous carrier, comprising:
    (a) introducing porous carrier into a first feeder;
    (b) continuously directing the porous carrier from the first feeder into a continuous blender, wherein the continuous blender comprises one or more nozzles;
    (c) continuously spraying a solution comprising an active pharmaceutical ingredient (API) dissolved in solvent into the continuous blender through the one or more nozzles to form API-impregnated porous carrier; and
    (d) continuously drying the API-impregnated porous carrier using a continuous dryer to form API-impregnated porous carrier in powder form; and
    wherein the process steps are applied in a single continuous fashion such that an output is maintained at a consistent rate with no need to stop production.

2. The continuous flow process of claim 1, wherein content variability of any single API in the powder has a relative standard deviation (RSD) of less than or equal to 3% when tested using samples of at least 200 mg of the dried API-impregnated porous carrier powder.

3. The continuous flow process of claim 1, wherein the porous carrier is directed into the continuous blender in step (b) at a feed rate of 1 kg/h to 200 kg/h.

4. The continuous flow process of claim 1, wherein the API solution is sprayed into the continuous blender in step (c) at a rate of less than 1 s$^{-1}$.

5. The continuous flow process of claim 1, wherein the continuous dryer of step (d) comprises a fluidized bed dryer having an air inlet temperature of 30° C. to 90° C.

6. The continuous flow process of claim 1, wherein the porous carrier is selected from magnesium aluminum metasilicate, granulated silicon dioxide, dibasic calcium phosphate, calcium hydrogen phosphate, and combinations thereof.

7. The continuous flow process of claim 1, wherein the porous carrier has a porosity of 20% to 85% pores by volume.

8. The continuous flow process of claim 1, wherein the porous carrier has an average pore size of 100 nm to 2000 nm.

9. The continuous flow process of claim 1, wherein the continuous process produces API-impregnated porous carrier powder that releases 50% of the API faster than a dry non-impregnated mixture of the API and the porous carrier.

10. A continuous flow process for manufacturing a pharmaceutical drug product from continuously manufactured API-impregnated porous carrier, comprising:
    (a) introducing porous carrier into a first feeder;
    (b) continuously directing the porous carrier from the first feeder into a continuous blender, wherein the continuous blender comprises one or more nozzles;
    (c) continuously spraying a solution comprising an active pharmaceutical ingredient (API) dissolved in solvent into the continuous blender through the one or more nozzles to form API-impregnated porous carrier;
    (d) continuously drying the API-impregnated porous carrier using a continuous dryer to form API-impregnated porous carrier powder; and
    (e) formulating the API-impregnated porous carrier powder into a finished pharmaceutical drug product; and
    wherein the process steps are applied in a single continuous fashion such that an output is maintained at a consistent rate with no need to stop production.

11. The continuous flow process of claim 10, wherein the finished pharmaceutical drug product is a solid oral dosage form.

12. The continuous flow process of claim 11, wherein the solid oral dosage form is selected from a tablet, capsule, powder, and granulate.

13. The continuous flow process of claim 10, wherein the continuous dryer is a fluidized bed dryer.

14. The continuous flow process of claim 10, wherein step (e) further comprises combining the powder with one or more pharmaceutically acceptable excipients selected from carriers, fillers, extenders, binders, humectants, disintegrating agents, absorption accelerators, wetting agents, controlled release agents, absorbents, lubricants, and coloring agents.

15. A continuous flow process for manufacturing a pharmaceutical drug product from active pharmaceutical ingredient (API) impregnated porous carrier, comprising:
    (a) continuously feeding the API-impregnated porous carrier formed in step (d) of claim 1 into a first feeder;
    (b) continuously combining the API-impregnated porous carrier with one or more pharmaceutically acceptable excipients to form a mixture, and
    (c) continuously compounding the mixture into a solid oral dosage form.

16. The continuous flow process of claim 15, wherein the API-impregnated porous carrier is capable of flowing through a feeder at a feed rate of 1 kg/h to 200 kg/h.

17. The continuous flow process of claim 15, wherein the solid oral dosage form is selected from a tablet, capsule, powder, and granulate.

18. The continuous flow process of claim 15, wherein the process is operated under closed loop control using a combination of sensors, controllers, and actuators to maintain the process within a desired range of operating parameters.

19. The continuous flow process of claim 15, wherein the API-impregnated porous carrier is prepared by a continuous manufacturing process.

* * * * *